US012700098B2

(12) United States Patent
Nayot et al.

(10) Patent No.: US 12,700,098 B2
(45) Date of Patent: Aug. 4, 2026

(54) SYSTEM AND METHOD FOR PREDICTING ENDOMETRIUM RECEPTIVITY

(71) Applicant: FUTURE FERTILITY INC., Toronto (CA)

(72) Inventors: Dan Nayot, Toronto (CA); Rene Michael Bharti, Toronto (CA); Alexandr Krivoi, Mississauga (CA); Jim Meriano, Mississauga (CA)

(73) Assignee: Future Fertility Inc., Toronto (CA)

( * ) Notice: Subject to any disclaimer, the term of this patent is extended or adjusted under 35 U.S.C. 154(b) by 307 days.

(21) Appl. No.: 18/566,601

(22) PCT Filed: Jun. 2, 2022

(86) PCT No.: PCT/CA2022/050881
§ 371 (c)(1),
(2) Date: Dec. 1, 2023

(87) PCT Pub. No.: WO2022/251962
PCT Pub. Date: Dec. 8, 2022

(65) Prior Publication Data
US 2024/0257351 A1     Aug. 1, 2024

Related U.S. Application Data

(60) Provisional application No. 63/195,719, filed on Jun. 2, 2021.

(51) Int. Cl.
*G06T 7/00*        (2017.01)
*A61B 5/00*        (2006.01)

(52) U.S. Cl.
CPC .......... *G06T 7/0016* (2013.01); *A61B 5/4325* (2013.01); *G06T 2207/10132* (2013.01);
(Continued)

(58) Field of Classification Search
CPC ......... G06T 7/0016; G06T 2207/10132; G06T 2207/20081; G06T 2207/20084; G06T 2207/30044; A61B 5/4325
See application file for complete search history.

(56) References Cited

U.S. PATENT DOCUMENTS 9,430,611 B2 *  8/2016  Rabinowitz ............ G16B 25/00
11,227,684 B2 *  1/2022  Kanan ................... G06T 7/0012
(Continued)

OTHER PUBLICATIONS

International Search Report and Written Opinion mailed Aug. 9, 2022 in International Application No. PCT/CA2022/050881.
(Continued)

*Primary Examiner* — Gregory M Desire
(74) *Attorney, Agent, or Firm* — Norton Rose Fulbright Canada LLP

(57) ABSTRACT
Methods and systems for predicting endometrium receptivity are disclosed, the method include: maintaining a data set representing a neural network having a plurality of weights; obtaining a first image of an endometrium with a first timestamp; extracting a first set of target endometrium features from the first image; and generating, using the neural network and based on the first set of target endometrium features, a predicted value indicating a endometrium receptivity of the endometrium in the first image.

20 Claims, 13 Drawing Sheets

(52) U.S. Cl.

CPC .............. *G06T 2207/20081* (2013.01); *G06T 2207/20084* (2013.01); *G06T 2207/30044* (2013.01)

(56) References Cited

U.S. PATENT DOCUMENTS

| | | | | |
|---|---|---|---|---|
| 11,705,226 | B2 * | 7/2023 | Colley .................... | G16B 40/00 |
| | | | | 705/3 |
| 11,741,365 | B2 * | 8/2023 | Khan .................... | G06N 3/0464 |
| | | | | 706/25 |
| 12,198,809 | B2 * | 1/2025 | Evans .................... | G16H 15/00 |
| 2023/0018456 | A1 * | 1/2023 | Erlich ...................... | G06N 7/01 |

OTHER PUBLICATIONS

The association between Clinical Pregnancy Rate in IVF-Cycles and Endometrial Receptivity based on a Novel Ultrasonographic Endometrial Receptivity Scoring System, Implantation and early pregnancy, Singh et al.

The effect of endometrial thickness and pattern measured by ultrasonography on pregnancy outcomes during IVF-ET cycles, Zhao et al. Reproductive Biology and Endocrinology 2012.

Ultrasound Based Endometrial Receptivity Scoring Improves In Vitro Fertilization Pregnancy Rates, Pierson et al., J Fertil In vitro IVF Worldw Reprod Med Genet Stem Cell Biol, vol. 9 Iss.6 No. 248, 2021.

What exactly is endometrial receptivity? Lessey et al., vol. 111 No. 4 / Apr. 2019.

A critical appraisal of studies on endometrial thickness and embryo transfer outcome, Mathyk et al., RBMO vol. 47 Issue 4 2023 103259.

Are endometrial parameters by three-dimensional ultrasound and power Doppler angiography related to in vitro fertilization/embryo transfer outcome? Merce et al., Fertility and Sterility vol. 89, No. 1, Jan. 2008.

Associations between endometrial microbiome and the local immune cell composition during the mid-secretory phase, Endometriosis and Endometrial Disorders, Ganeva et a.

Clinical impact of personalized embryo transfer (pET) guided by endometrial receptivity analysis (ERA) in patients with ≥ 1 failed transfers, Session 20: Poster discussion session—Endometriosis and Endometrial Disorders, Ruiz-Alonso et al.

Continuous endometrial volumetric analysis for endometrial receptivity assessment on assisted reproductive technology cycles, Martins et al. BMC Pregnancy and Childbirth (2020).

Deep learning analysis of endometrial histology as a promising tool to predict the chance of pregnancy after frozen embryo transfers, Li et al., The Author(s), under exclusive licence to Springer Science+Business Media, LLC, part of Springer Nature 2023.

Effect of the endometrial thickness on the live birth rate: insights from 959 single euploid frozen embryo transfers without a cutoff for thickness, Ata et al., 2023 by American Society for Reproductive Medicine.

Endometrial eubiosis vs dysbiosis: what role does the abundance of Lactobacillus play in endometrial receptivity? Implantation and early pregnancy, Sánchez et al.

Endometrial receptivity in women with endometriosis undergoing Assisted Reproductive Technology (ART) after frozen embryo transfer: a matched pair case-control study, Endometriosis and Endometrial Disorders, Casalechi et al.

An endometrial receptivity scoring system evaluated by ultrasonography in patients undergoing frozen-thawed embryo transfer: a prospective cohort study, Session 27: Poster discussion session—Implantation and Early Pregnancy, Yan et al.

Endometrial thickness as a predictor of live birth and perinatal outcomes following oocyte donation, Session 46: Clinical and laboratory prognostic factors in ART, Santos-Ribeiro et al.

Impact of endometrial receptivity analysis on pregnancy outcomes In patients undergoing embryo transfer: A systematic review and meta-analysis, Implantation and early pregnancy, Irene et al.

Impact of Endometrial Receptivity Analysis on Pregnancy Outcomes In Patients Undergoing Embryo Transfer: A Systematic Review and Meta-Analysis, Zolfaroli et al., The Author(s), under exclusive licence to Springer Science +Business Media, LLC, part of Springer Nature 2023, corrected publication 2023.

Artificial Intelligence in the Assessment of Female Reproductive Function Using Ultrasound, Chen et al., 2021 The Authors. Journal of Ultrasound in Medicine published by Wiley Periodicals LLC on behalf of American Institute of Ultrasound in Medicine.

Numeric Embryo Quality Scoring Index (NEQsi) is Predictive of IVF Cycle Outcome at any Endometrial Thickness, Embryology, Pierson et al.

Optimal timing of ultrasonographic and Doppler evaluation of uterine receptivity to implantation, Dechaud et al., vol. 16. No 3. 2008 368-375 Reproductive BioMedicine Online; www.rbmonline.com/Article/3055 on web Jan. 21, 2008.

Performance of ERA test after PGT-A in RIF patients defined according to ESHRE 2023 good practice recommendations: a retrospective case-control study, Implantation and early pregnancy, Golino et al.

The science of implantation emerges blinking into the light, Sharkey et al., Reproductive BioMedicine Online (2013).

Should we continue to measure endometrial thickness in modern-day medicine? The effect on live birth rates and birth weight, Ribeiro et al., 1472-6483/© 2018 Reproductive Healthcare Ltd. Published by Elsevier Ltd.

* cited by examiner

110

Input Layer    Hidden Layer    Output Layer

SYSTEM AND METHOD FOR PREDICTING ENDOMETRIUM RECEPTIVITY

CROSS-REFERENCE TO RELATED APPLICATION

This application claims the benefit of and priority to U.S. provisional patent application No. 63/195,719, filed on Jun. 2, 2021, the entire content of which is herein incorporated by reference.

FIELD

This disclosure relates to systems for predicting endometrium receptivity, which indicates if an endometrial cavity is receptive for an embryo to implant and develop. More specifically, this disclosure relates to systems for predicting endometrium receptivity based on ultrasound images of the endometrial cavity.

BACKGROUND

In patients that undergo an embryo transfer, there is no validated non-invasive tool that can accurately predict whether or not the endometrium is receptive, which is a pre-requisite for a successful implantation and progress into a viable pregnancy. Ultrasound images of the endometrium are routinely used during an embryo transfer cycle, and the endometrial thickness is a clinical variable that is used to determine whether or not to proceed with an embryo transfer. For example, if the endometrial lining is below a certain thickness, the embryo transfer cycle might be cancelled. Therefore, there is a need to better evaluate an ultrasound image of the endometrium that provides improved accuracy to aid patients and clinicians to decide whether or not to proceed with a scheduled embryo transfer.

SUMMARY

In one aspect, the present disclosure may provide computer-implemented system for predicting endometrium receptivity based on ultrasound images of the endometrial cavity, the system may include: a processor; and a memory coupled to the processor and storing processor-executable instructions that, when executed, configure the processor to: maintain a data set representing a neural network having a plurality of weights; obtain a first image of an endometrium with a first timestamp; extract a first set of target endometrium features from the first image; and generate, using the neural network and based on the first set of target endometrium features, a predicted value indicating a endometrium receptivity of the endometrium in the first image.

In some embodiments, the processor-executable instructions, when executed, further configure the processor to generate a value representative of a likelihood of a successful embryo implantation.

In some embodiments, the first set of target endometrium features comprises at least one of: a thickness of the endometrium, a length of the endometrium, a surface area of the endometrium, and a pattern of the endometrium.

In some embodiments, the pattern of the endometrium comprises a trilaminar pattern.

In some embodiments, the processor-executable instructions, when executed, configure the processor to: receive a second image of the endometrium with a second timestamp; extract a second set of target endometrium features from the second image; and generate, using the neural network and based on the first and second sets of target endometrium features, the predicted value indicating the endometrium receptivity of the endometrium.

In some embodiments, the second set of target endometrium features comprises at least one of: a thickness of the endometrium, a length of the endometrium, a surface area of the endometrium, and a pattern of the endometrium.

In some embodiments, the pattern of the endometrium comprises a trilaminar pattern.

In some embodiments, the first timestamp and the second timestamp is at least four days apart.

In some embodiments, the processor-executable instructions, when executed, configure the processor to: determine a difference between the first image and the second image; and analyze the difference to generate the predicted value indicating the endometrium receptivity of the endometrium.

In some embodiments, the first image and the second image are transvaginal images.

In some embodiments, the neural network comprises a convolutional neural network.

In some embodiments, the predicted value indicating the endometrium receptivity comprises a probability value.

In some embodiments, the processor-executable instructions, when executed, configure the processor to, prior to extracting the first set of target endometrium features, pre-process the first image by normalizing image brightness values, cropping irrelevant parts of an image, removing noise, or performing image sharpening.

In some embodiments, the neural network is trained based on a set of training data comprising: a plurality of ultrasound images of one or more endometria, each of the plurality of ultrasound images showing a respective endometrium; and for each of the plurality of ultrasound images, a respective label indicating an outcome of a respective embryo implantation in the respective endometrium in the respective ultrasound image.

In some embodiments, each of the plurality of ultrasound images is associated with training data comprising a blastocyst quality of an embryo transferred into a respective endometrial cavity in the respective ultrasound image.

In some embodiments, the processor-executable instructions, when executed, configure the processor to, during training of the neural network, pre-process the plurality of ultrasound images by performing at least one of: image flipping, image rotating or image cropping.

In some embodiments, each of the plurality of ultrasound images is associated with training data comprising one or more of: a patient ID, a patient age, a cycle ID, date of ultrasound, and date of transfer.

In some embodiments, the first image is received from an ultrasound machine.

In accordance with another aspect, there is a computer-implemented method for predicting endometrium receptivity, the method may include: maintaining a data set representing a neural network having a plurality of weights; obtaining a first image of an endometrium with a first timestamp; extracting a first set of target endometrium features from the first image; and generating, using the neural network and based on the first set of target endometrium features, a predicted value indicating a endometrium receptivity of the endometrium in the first image.

In some embodiments, the method may further include: generating a value representative of a likelihood of a successful embryo implantation.

In some embodiments, the first set of target endometrium features comprises at least one of: a thickness of the endometrium, a length of the endometrium, a surface area of the endometrium, and a pattern of the endometrium.

In some embodiments, the method may further include: receiving a second image of the endometrium with a second timestamp; extracting a second set of target endometrium features from the second image; and generating, using the neural network and based on the first and second sets of target endometrium features, the predicted value indicating the endometrium receptivity of the endometrium.

In some embodiments, the second set of target endometrium features comprises at least one of: a thickness of the endometrium, a length of the endometrium, a surface area of the endometrium, and pattern of the endometrium.

In some embodiments, the first timestamp and the second timestamp is at least four days apart.

In some embodiments, the method may further include: determining a difference between the first image and the second image; and analyzing the difference to generate the predicted value indicating the endometrium receptivity of the endometrium.

In some embodiments, the first image and the second image are transvaginal images.

In some embodiments, the neural network comprises a convolutional neural network.

In some embodiments, the predicted value indicating the endometrium receptivity comprises a probability value.

In some embodiments, the method may further include: prior to extracting the first set of target endometrium features, pre-processing the first image by performing at least one of: normalizing image brightness values, cropping irrelevant parts of an image, removing noise, or image sharpening.

In some embodiments, the neural network is trained based on a set of training data comprising: a plurality of ultrasound images of one or more endometria, each of the plurality of ultrasound images showing a respective endometrium; and for each of the plurality of ultrasound images, a respective label indicating an outcome of a respective embryo implantation in the respective endometrium in the respective ultrasound image.

In some embodiments, each of the plurality of ultrasound images is associated with training data comprising a blastocyst quality of an embryo transferred into a respective endometrial cavity in the respective ultrasound image.

In some embodiments, the processor-executable instructions, when executed, configure the processor to, during training of the neural network, pre-process the plurality of ultrasound images by performing at least one of: image flipping, image rotating or image cropping.

In some embodiments, each of the plurality of ultrasound images is associated with training data comprising one or more of: a patient ID, a patient age, a cycle ID, date of ultrasound, and date of transfer.

In accordance with yet another aspect, there is non-transitory computer-readable medium having stored thereon machine interpretable instructions which, when executed by a processor, cause the processor to perform: maintaining a data set representing a neural network having a plurality of weights; obtaining a first image of an endometrium with a first timestamp; extracting a first set of target endometrium features from the first image; and generating, using the neural network and based on the first set of target endometrium features, a predicted value indicating a endometrium receptivity of the endometrium in the first image.

Many further features and combinations thereof concerning embodiments described herein will appear to those skilled in the art following a reading of the present disclosure.

BRIEF DESCRIPTION OF THE DRAWINGS

In the figures, embodiments are illustrated by way of example. It is to be expressly understood that the description and figures are only for the purpose of illustration and as an aid to understanding.

DETAILED DESCRIPTION

Figure 1:
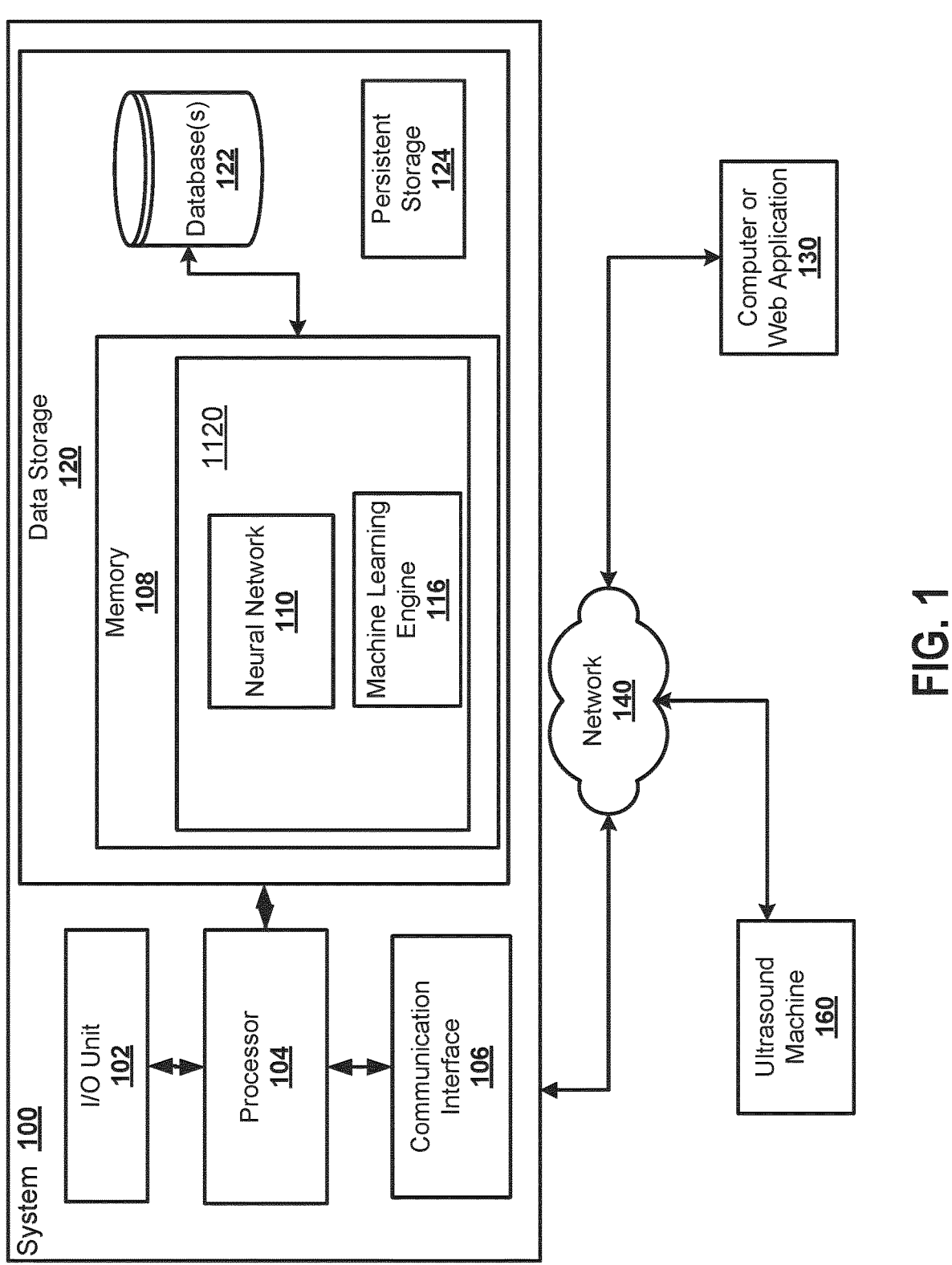
FIG. 1 is a schematic diagram of a computer-implemented system for predicting endometrium receptivity, in accordance with an embodiment.

The present disclosure may describe various embodiments using machine learning systems to conduct a non-invasive image analysis to determine likelihood of successful implantation (e.g., attachment and development) of an embryo to an endometrial surface of the uterus and then becoming a viable pregnancy. In some embodiments, the machine learning system may be used to evaluate one or more ultrasound images of the endometrium. The system may be a non-invasive, real-time, automated, and reproducible tool in fertility treatment.

As a preliminary matter, some of the figures describe concepts in the context of one or more structural components, variously referred to as functionality, modules, features, elements, etc. The various components shown in the figures can be implemented in any manner, for example, by software, hardware (e.g., discrete logic components, etc.), firmware, and so on, or any combination of these implementations. In one embodiment, the various components may reflect the use of corresponding components in an actual implementation.

In other embodiments, any single component illustrated in the figures may be implemented by a number of actual components. The depiction of any two or more separate components in the figures may reflect different functions performed by a single actual component. The figures discussed below provide details regarding exemplary systems that may be used to implement the disclosed functions.

Some concepts are described in form of steps of a process or method. In this form, certain operations are described as being performed in a certain order. Such implementations are exemplary and non-limiting. Certain operations described herein can be grouped together and performed in a single operation, certain operations can be broken apart into plural component operations, and certain operations can be performed in an order that differs from that which is described herein, including a parallel manner of performing the operations. The operations can be implemented by software, hardware, firmware, manual processing, and the like, or any combination of these implementations. As used herein, hardware may include computer systems, discrete logic components, such as application specific integrated circuits (ASICs) and the like, as well as any combinations thereof.

As to terminology, the phrase "configured to" encompasses any way that any kind of functionality can be constructed to perform an identified operation. The functionality can be configured to perform an operation using, for instance, software, hardware, firmware and the like, or any combinations thereof.

As utilized herein, terms "component," "system," "client" and the like are intended to refer to a computer-related entity, either hardware, software (e.g., in execution), and/or firmware, or a combination thereof. For example, a component can be a process running on a processor, an object, an executable, a program, a function, a library, a subroutine, and/or a computer or a combination of software and hardware.

By way of illustration, both an application running on a server and the server can be a component. One or more components can reside within a process and a component can be localized on one computer and/or distributed between two or more computers. The term "processor" is generally understood to refer to a hardware component, such as a processing unit of a computer system.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any non-transitory computer-readable device, or media.

Non-transitory computer-readable storage media can include but are not limited to magnetic storage devices (e.g., hard disk, floppy disk, and magnetic strips, among others), optical disks (e.g., compact disk (CD), and digital versatile disk (DVD), among others), smart cards, and flash memory devices (e.g., card, stick, and key drive, among others). In contrast, computer-readable media generally (i.e., not necessarily storage media) may additionally include communication media such as transmission media for wireless signals and the like.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Example embodiments described herein provide methods and systems that can perform a single image analysis of an endometrium to provide a predicted value indicating whether the endometrium is most likely ready for an embryo transfer, and therefore does not require prolonged exposure. That is, exemplary systems and methods provide insight into likelihood of reaching a reproductive milestone based on one singular image of an endometrium to aid in making a decision on timing related to implanting a potential embryo. Therefore, in an exemplary embodiment, exemplary methods and systems provide a non-invasive, accurate, and fast approach for predicting success rates of potential outcomes of an embryo implant in an endometrium.

In some embodiments, a second image of the endometrium is provided, enabling the system to provide an improved prediction of whether the endometrium is most likely ready for a successful embryo implantation based on both the first and second images of the endometrium. The second image may be taken the day before the planned embryo transfer, or on the day of the planned embryo transfer.

In an exemplary embodiment, implantation may refer to a process by which the embryo may attach to the endometrial surface of the uterus (apposition and adhesion) and may invade the epithelium (invasion) to establish a connection with the maternal circulation to establish a placenta. In simple terms, implantation may be a result of a "viable" embryo being presented to a "receptive" endometrium during the "window of implantation" (WOI). The phrase "a value for endometrium receptivity" may therefore refer to a value indicating how likely an embryo will successfully implant and attach to the endometrial surface of the uterus. A high value for endometrium receptivity may indicate a higher endometrium receptivity and thus a higher likelihood of a successful embryo implantation, whereas a low value for endometrium receptivity may indicate a lower endometrium receptivity and thus a lower likelihood of a successful embryo implantation.

In some embodiments, the value for endometrium receptivity may be presented as a percentage or a probability, and a threshold (e.g., 80%) may be predefined indicating a minimum value for endometrium receptivity required for a successful embryo implantation.

In an exemplary embodiment, concept of window implantation may refer to a time period that occurs 5-10 days after Luteinizing Hormone (LH) surge or Day 16-22 of a 28 day reproductive cycle or 4-7 days after progesterone treatment.

Exemplary embodiments of computer system may utilize machine learning techniques to assist with image analysis, in order to provide exemplary automated and accurate endometrium classification system. The exemplary classification and predictions may serve as a clinically valuable tool in determining when to implant an embryo in a uterus which may lead to the highest chance of successful attachment to endometrium and lead to a clinical pregnancy.

In an exemplary embodiment, a potential embryo with a high likelihood of reaching reproductive milestones may be chosen. Then, an ultrasound of a patient's uterus may be captured. In an exemplary embodiment, the image may focus on the endometrium and the endometrium may be analyzed.

Utilizing developed parameters for both processing and analyzing images as discussed in further detail below, artificial intelligence (e.g., machine learning engines) may be utilized to determine the likelihood of potential successful outcomes with respect to the potential embryo in the current state of the endometrium, by utilizing the image of the endometrium. In an exemplary embodiment, an exemplary validation score or prediction may be provided. Additionally, exemplary supportive metrics may be provided, which may include chance of success and confidence in prediction, aiding a clinician in providing advice and guidance to potential patients on medical approaches.

In an exemplary embodiment, a clinician may therefore decide whether to continue with implanting the embryo immediately, wait an additional amount of time to reevaluate the endometrium to whether it gives the best chance of successfully reaching reproductive milestones, or to cancel the cycle and try again in a subsequent cycle.

FIG. 1 is a schematic diagram of a computer-implemented system 100 for predicting endometrium receptivity, in accordance with an embodiment. A predicted value for endometrium receptivity may be used as a metric for determining or estimating a likelihood or potential of an embryo to become attached to an endometrium of a uterus or to lead to clinical pregnancy. Endometrium is lining of a uterus. Typically, each month, as part of the menstrual cycle, the body prepares the endometrium to host an embryo.

A machine learning application 1120 can maintain a neural network 110 to perform actions based on input data, which may include at least a single image of an endometrium. An example action may be a prediction. The machine learning application 1120 may include a machine learning engine 116 that is implemented to use a suitable machine learning technique to train a neural network 110, which may be, for example, a Convolutional Neural Network (CNN).

Figure 2:
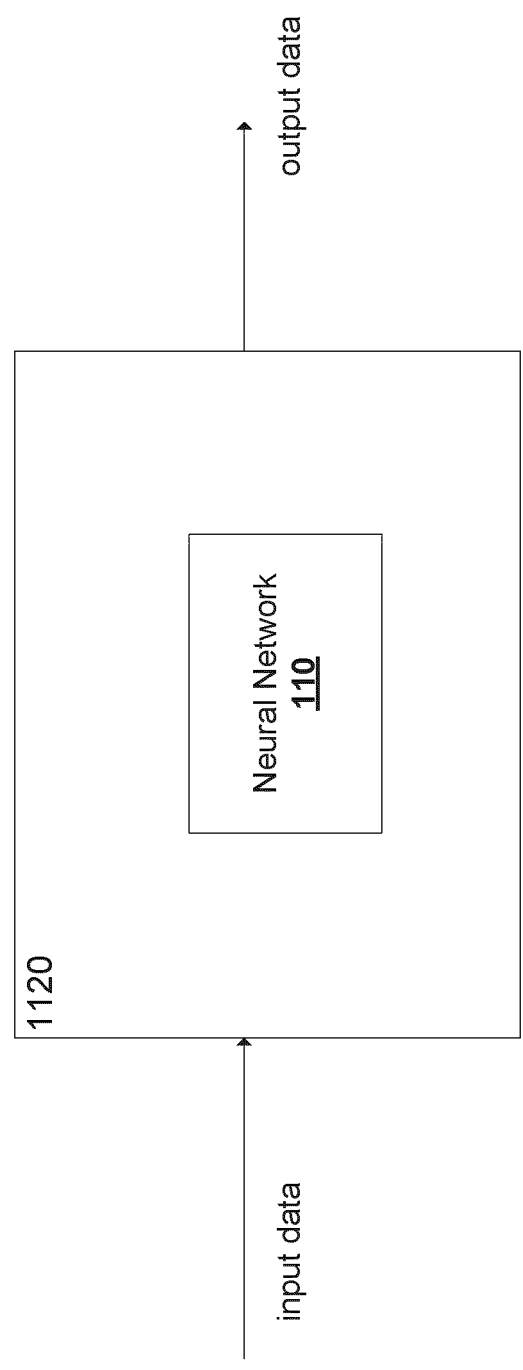
FIG. 2 illustrates a system for machine learning architecture, in accordance with an embodiment of the present disclosure.

FIG. 2 shows an example neural network 110 being trained by a machine learning application 1120. Once the machine learning application 1120 has been trained, it generates output data reflective of its decisions to take particular actions (e.g., make a prediction) in response to particular input data. Input data may include one or more ultrasound images, while output data may include a predicted value for endometrium receptivity, which may be used as a metric for determining or estimating a likelihood or potential of an embryo to become attached to an endometrium of a uterus or to lead to clinical pregnancy. The output, which is the predicted value for endometrium receptivity, may be a probability value. For instance, the output may be a probability of 60% that the endometrium will have a successful embryo implantation.

The neural network 110, which may be a CNN 110, may be constructed as a Residual Learning (ResNet) model. In some embodiments, the neural network 110 may be implemented using a ResNet50 architecture (a variant of ResNet model), which has 48 convolution layers along with 1 MaxPool and 1 Average Pool layer. It can have $3.8 \times 10^9$ Floating points operations.

In some embodiments, neural network 110 is a convolutional neural network that is pre-trained on more than a million images from an image database. The network can be 50 layers deep and can classify images into 1000 object categories, such as keyboard, mouse, pencil, and many animals. As a result, neural network 110 has learned rich feature representations for a wide range of images. Then this network can be fine-tuned on images of endometrium and outcome labels to predict an implantation outcome.

In some embodiments, during training of the neural network 110, pre-processing may be performed on the plurality of ultrasound images including: image flipping, image rotating or image cropping.

Figure 3:
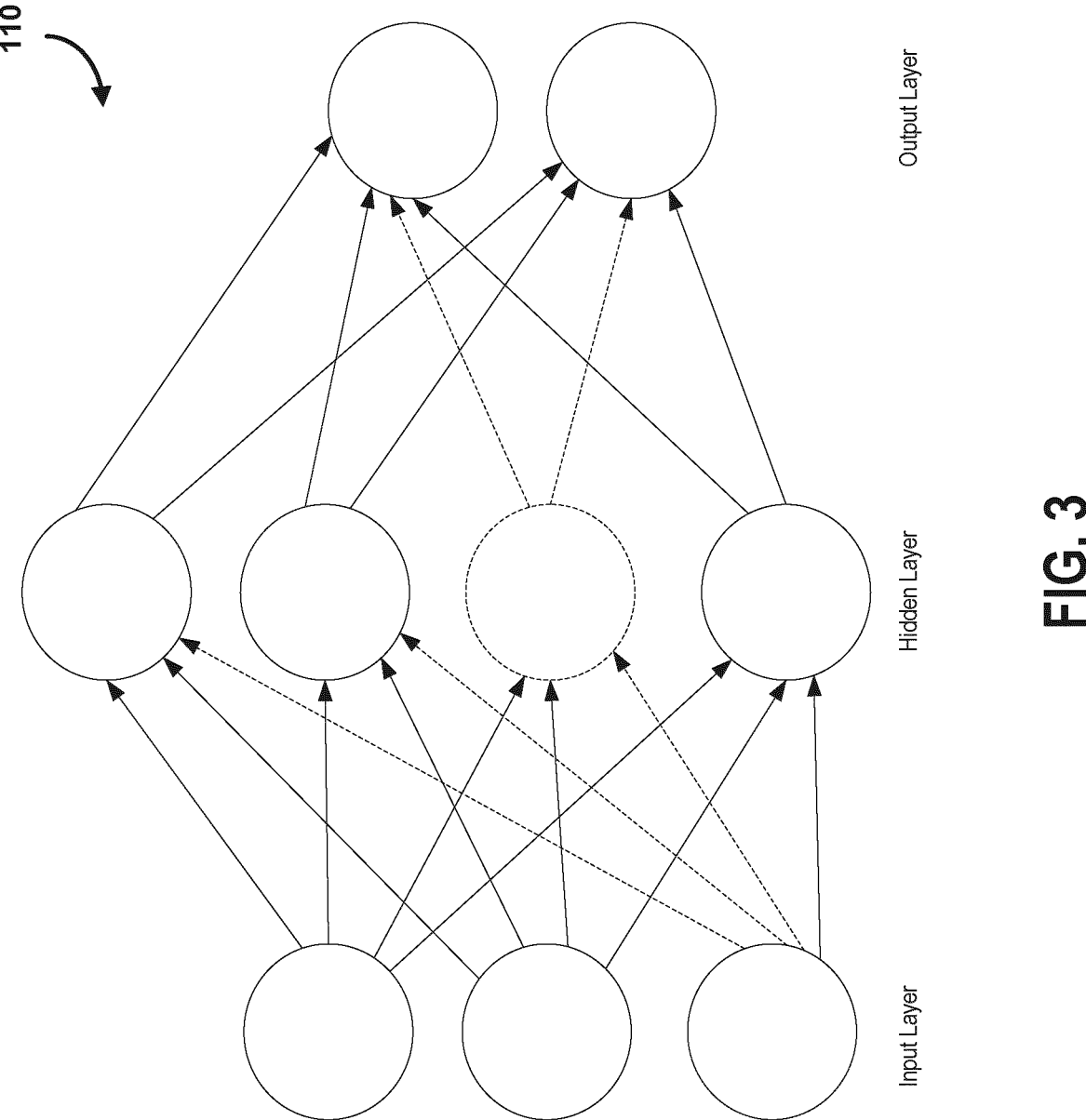
FIG. 3 is a schematic diagram of an example neural network, in accordance with an embodiment.

FIG. 3 is a schematic diagram of an example neural network 110, in accordance with an embodiment. The example neural network 110 can include an input layer, a hidden layer, and an output layer. The neural network 110 processes input data using its layers based on machine learning, for example.

Referring back to FIG. 1, System 100 includes an I/O unit 102, a processor 104, a communication interface 106, and a data storage 120. I/O unit 102 enables system 100 to interconnect with one or more input devices, such as a keyboard, mouse, camera, touch screen and a microphone, sensors 160, and/or with one or more output devices such as a display screen and a speaker.

Processor 104 executes instructions stored in memory 108 to implement aspects of processes described herein. For example, processor 104 may execute instructions in memory 108 to configure a data collection unit, interface unit (to provide control commands to interface application 130), neural network 110, machine learning application 1120, machine learning engine 116, and other functions described herein.

Processor 104 can be, for example, various types of general-purpose microprocessor or microcontroller, a digital signal processing (DSP) processor, an integrated circuit, a field programmable gate array (FPGA), a reconfigurable processor, or any combination thereof.

Communication interface 106 enables system 100 to communicate with other components, to exchange data with other components, to access and connect to network resources, to serve applications, and perform other computing applications by connecting to a network 140 (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g., Wi-Fi or WiMAX), SS7 signaling network, fixed line, local area network, wide area network, and others, including any combination of these.

Data storage 120 can include memory 108, databases 122, and persistent storage 124. Data storage 120 may be configured to store information associated with or created by the components in memory 108 and may also include machine executable instructions. Persistent storage 124 implements one or more of various types of storage technologies, such as solid state drives, hard disk drives, flash memory, and may be stored in various formats, such as relational databases, non-relational databases, flat files, spreadsheets, extended markup files, etc.

Data storage 120 stores a model for a machine learning neural network 110. The neural network 110 is trained and used by a machine learning application 1120 to generate one or more predicted data values based on one or more ultrasound images, which may be transmitted from an ultrasound machine 160 or from a database 122.

Memory 108 may include a suitable combination of any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like.

Figure 6:
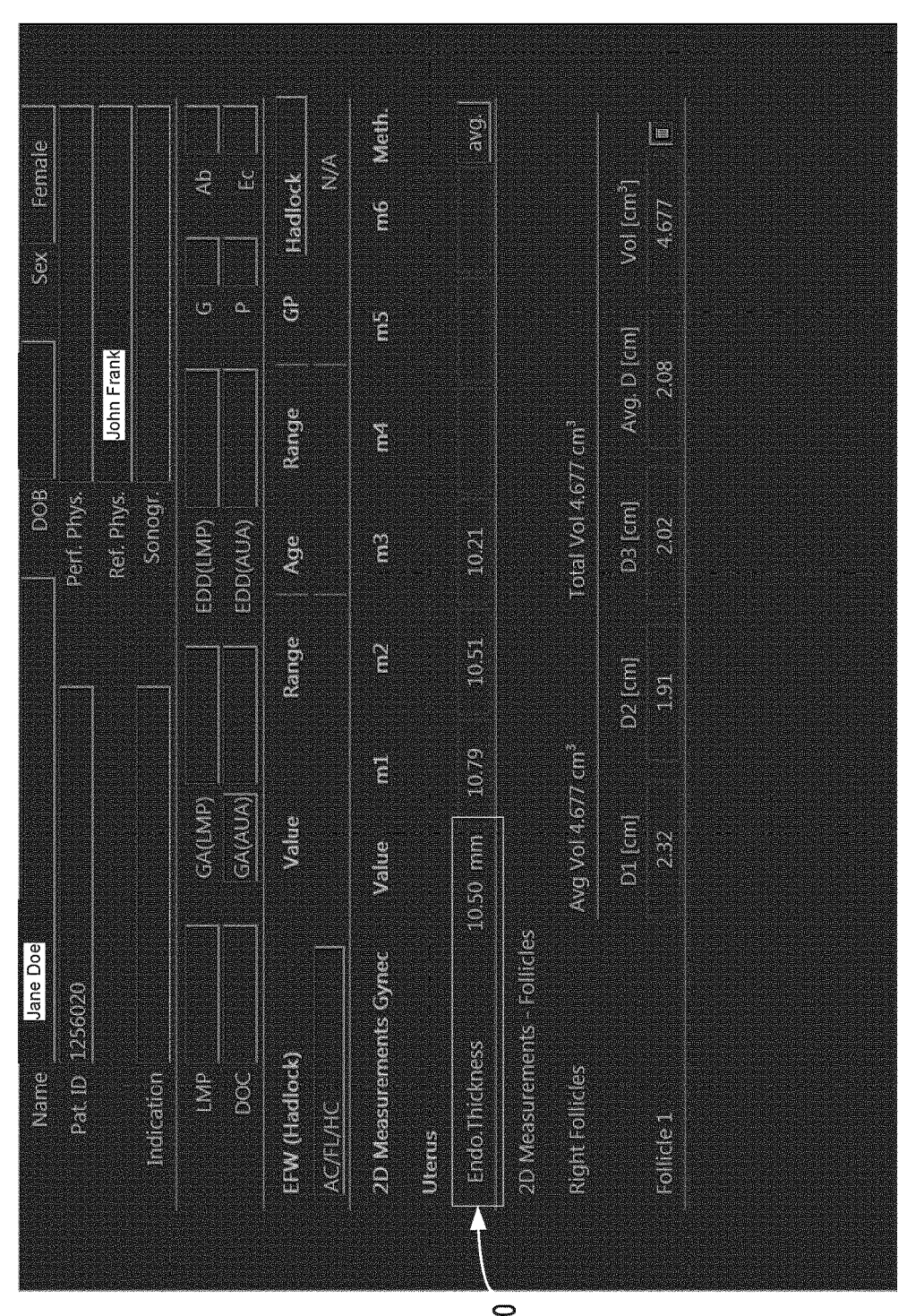
FIG. 6 shows an example user interface of an ultrasound machine during a transvaginal ultrasound scan, in accordance with embodiments of the present disclosure.

System 100 may connect to a computer or web-based application 130 accessibly by a user device. The application 130 interacts with the system 100 to exchange data (including control commands) and generates visual elements for display at the user device. The visual elements can represent machine learning networks 110 and output generated by machine learning networks 110. The visual elements may represent elements on a graphical user interface 600 as shown in FIG. 6, for example.

System 100 may be operable to register and authenticate users (using a login, unique identifier, and password for example) prior to providing access to applications, a local network, network resources, other networks and network security devices.

System 100 may connect to different data sources including ultrasound machine 160 to receive input data such as one or more ultrasound images.

Processor 104 is configured to execute machine executable instructions (which may be stored in memory 108) to maintain a neural network 110, and to train neural network 110 of using machine learning engine 116. The machine learning engine 116 may implement various machine learning algorithms, such as CNN models such as ResNet50, other suitable models, or statistical algorithms.

In some example embodiments, a process for training the neural network 110 includes, as a first step, receiving a plurality of ultrasound images and their respective labels as a training data set.

For example, the training data set may include: a plurality of ultrasound images of one or more endometria, each of the plurality of ultrasound images showing a respective endometrium; and for each of the plurality of ultrasound images, a respective label indicating an outcome of a respective embryo implantation in the respective endometrium in the respective ultrasound image.

In some embodiments, each of the plurality of ultrasound images is associated with training data (e.g., as part of feature data) comprising a blastocyst quality of an embryo transferred into a respective endometrial cavity in the respective ultrasound image. For example, negative influence of a bad embryo in the resulting non-implantation may be filtered out by limiting the blastocyst quality to a certain value or a range of values.

In some embodiments, each of the plurality of ultrasound images is associated with training data (e.g., as part of feature data) comprising one or more of: a patient ID, a patient age, a cycle ID, date of ultrasound, and date of transfer.

Each ultrasound image and its respective label outcome may be supplemented with supplemental data including patient ID, cycle ID, date of the ultrasound and date of transfer.

In some embodiments, the training data set may be retrieved from a first database 122 containing a set of images related to a plurality of endometrium and associated reproductive milestone data. In an exemplary embodiment, the reproductive milestone data may refer to data related to embryo implantation and clinical pregnancy, wherein the data indicates whether the endometrium may have reached a particular reproductive milestone or not. In an exemplary embodiment, a plurality of images associated with each of the plurality of endometrium may be included in the set of images.

For example, a first ultrasound may be captured of an endometrium, then various images of the endometrium may be captured as a thickness of a respective endometrium changes. In an exemplary embodiment, a respective thickness may change throughout the different phases of the menstrual cycle (or in the estrogen or progesterone dominant phase). There may be associated data on when an embryo was implanted in the endometrium and the ending result, for example, whether the embryo attached or not (based on BHCG blood test result), or whether a full clinically pregnancy occurred (based on an early obstetrical ultrasound). Accordingly, the associated data may indicate whether each reproductive milestone for that particular embryo was successful or not. For example, embryo implantation, and whether clinical pregnancy was successful or not. In exemplary embodiments, the data may be parsed so that any influence on the data due to poor embryo quality is minimized by taking in to account embryo quality information.

In some embodiments, the images may be captured with an image capturing device, such as an ultrasound machine 160. The image capturing techniques are not completely standardized, and there is a significant technician-dependent variability, but there are accepted general guidelines how to capture this image on ultrasound. The endometrium should be measured in the long axis or sagittal plane, ideally on transvaginal scanning, with the entirety of the endometrial lining through to the endocervical canal in view. The measurement is of the thickest echogenic area from one basal endometrial interface across the endometrial canal to the other basal surface.

Ultrasound Images (e.g., FIGS. 7A to 7C) are usually greyscale but images in color can also be used. Resolution of an example ultrasound image can have at least 300 pixels on side.

In some embodiments, a plurality of images of an endometrium may be captured or a video may be captured from which a series of images may be extracted. In an exemplary embodiment, other type of images such as an MRI may be captured. When the source data is a video, the plurality of images may be generated based on video sequence data captures according to certain rules.

In some embodiments, during training of the neural network, captured images may go through a process of data augmentation, where the images may be transformed by one or more of scaling, rotating, flipping, and adjusting pixel values. In an exemplary embodiment, data augmentation may allow for standardization of the all the captured images. In an exemplary embodiment, standardizing all the captured images to user defined or automatically generated parameters may be valuable in terms of improving predictive accuracy.

In some embodiments, creating a clean and unbiased training dataset may serve as a critical part of developing a robust predictive model. A clean and unbiased data set may refer to both image quality and data linking, that is, an accurate record of images and reproductive outcomes. In an exemplary embodiment, any images with undesirable qualities such as debris, shadowing, poor exposure, etc., may be removed from respective datasets. In an exemplary embodiment, images associated with patients that may have uterine fibroids or adenomyosis, or anything that may cause the image of the endometrium to be sub-optimal, may be excluded.

As discussed above, the first set of data may include images of endometria and respective reproductive milestone outcomes associated with embryos implanted within the endometrium. The outcome of each embryo used in an exemplary dataset may be accounted for, embryo transfer to clinical pregnancy, thus producing a clean dataset. In an exemplary embodiment, information regarding the implanted embryos may include predictions regarding success of reaching reproductive milestones for an embryo, such as a successful implantation (a positive BHCG pregnancy test) and clinical pregnancy (ultrasound evidence of a fetal heart rate). A large pool of endometrium images may be retrieved which may entail multiple images captured over a period of a few days for each respective endometrium.

In some embodiments, the captured image may be cropped with the object of interest (endometrium) in the center. For example, an image may be cropped to a resolution of 230 by 230 pixels or other relevant dimensions with a potential endometrium in the center of the cropped image, though it is not necessary for the endometrium to be placed in the center of the cropped image. In some embodiments, the images may be cropped to remove irrelevant parts or pixels.

In some embodiments, only ultrasound images associated with a range of a blastocyst quality are selected for training the neural network 110. The ultrasound images may each have a timestamp, which may include a date and a time indicating when the respective ultrasound image is taken. The training data set may include at least a first group or set of ultrasound images dated before a patient or user takes progesterone, which is likely 5-6 days before a planned embryo transfer. This first group or set of ultrasound images may be transvaginal ultrasound images.

The training data set may further include a second group or set of ultrasound images dated 3-5 days after a patient or user takes progesterone, but a day before a planned embryo transfer. This second group or set of ultrasound images may be transvaginal ultrasound images.

In some embodiments, the second group or set of ultrasound images may be dated after a patient or user takes progesterone, but on the day of the planned embryo transfer. This second group or set of ultrasound images may be abdominal or transvaginal ultrasound images.

Figure 8A:
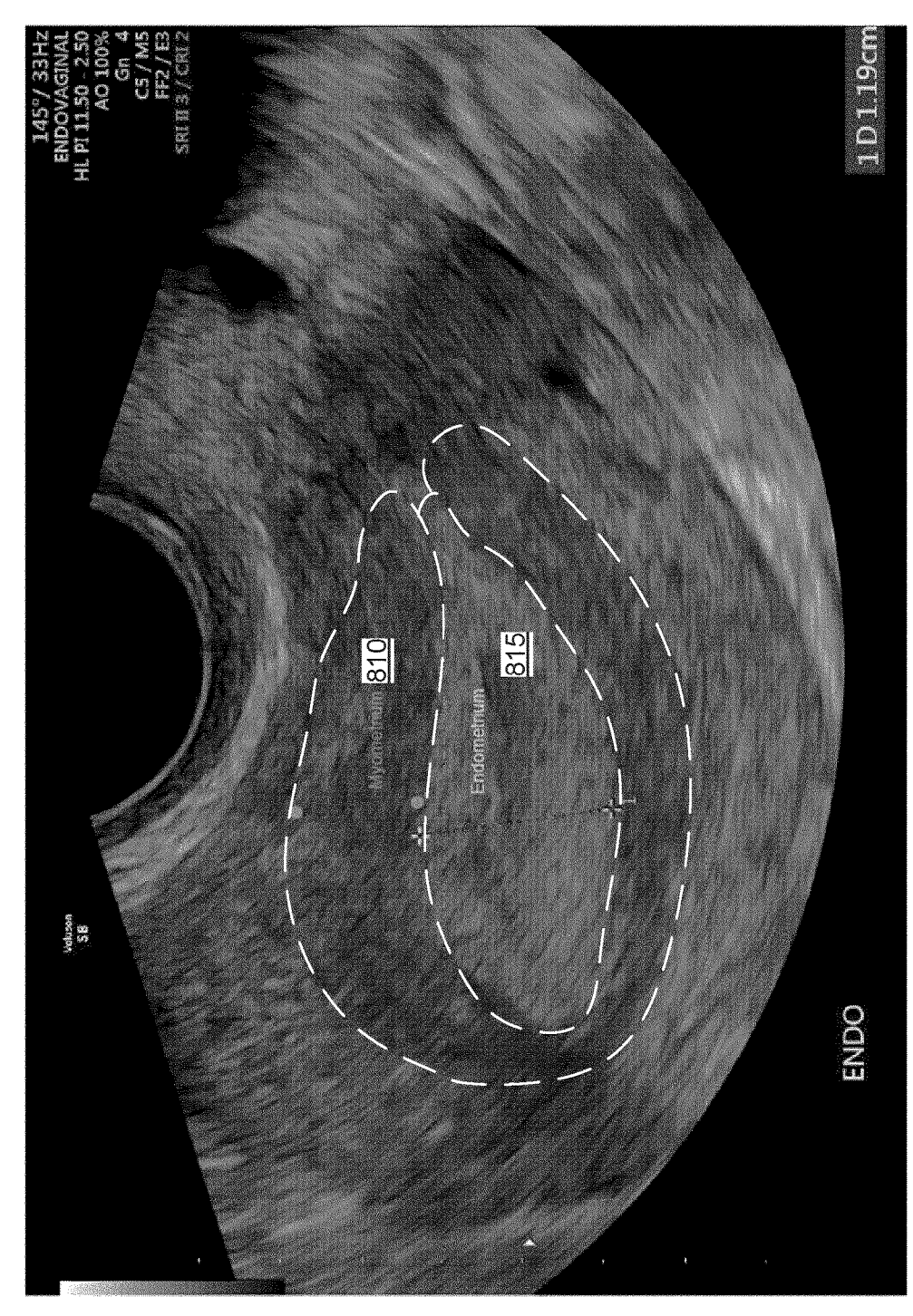
FIGS. 8A and 8B shows two example ultrasound images showing an endometrium, taken after treatment of progesterone but before the day of embryo transfer, in accordance with embodiments of the present disclosure.
Figure 8B:
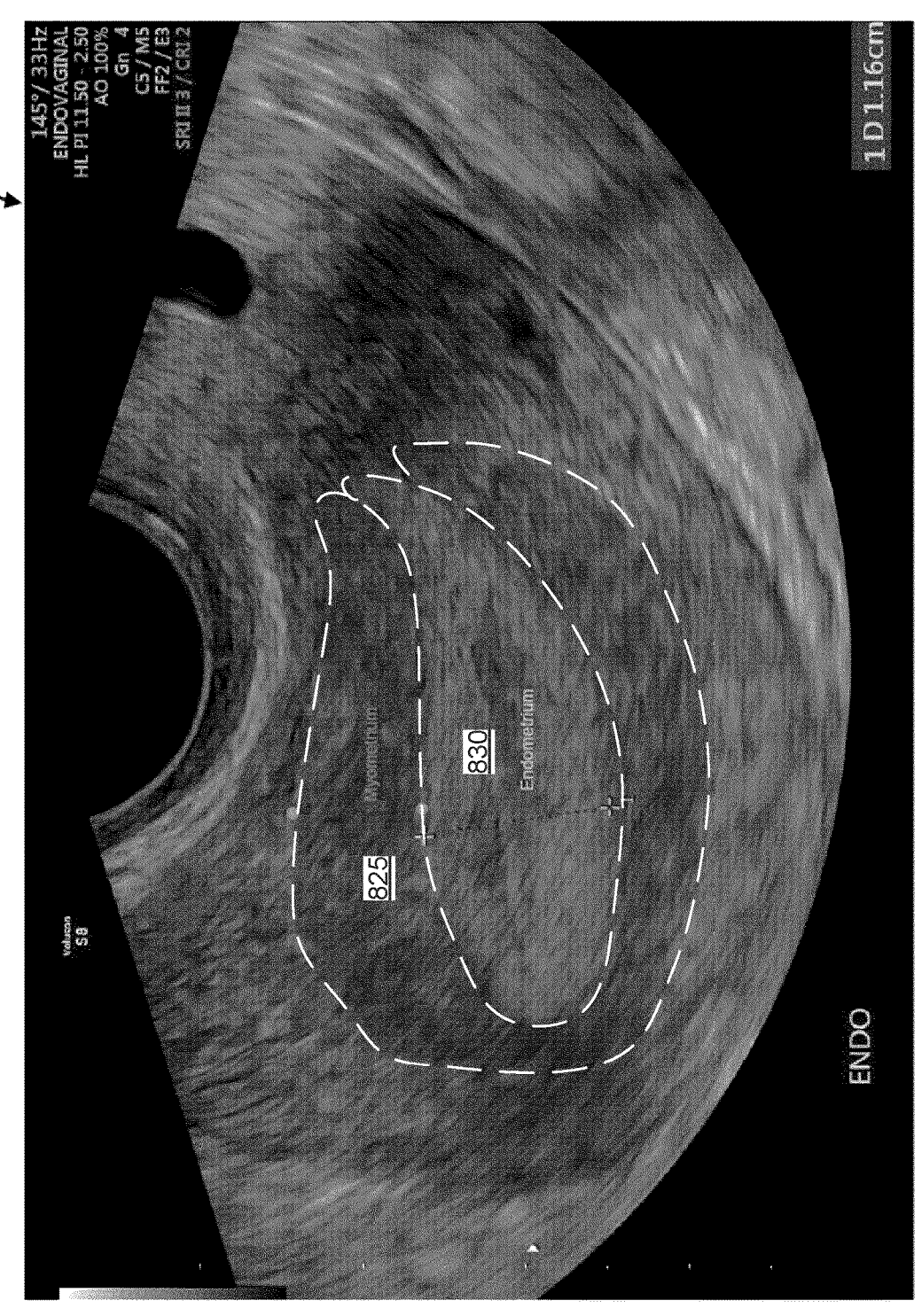
Figure 9A:
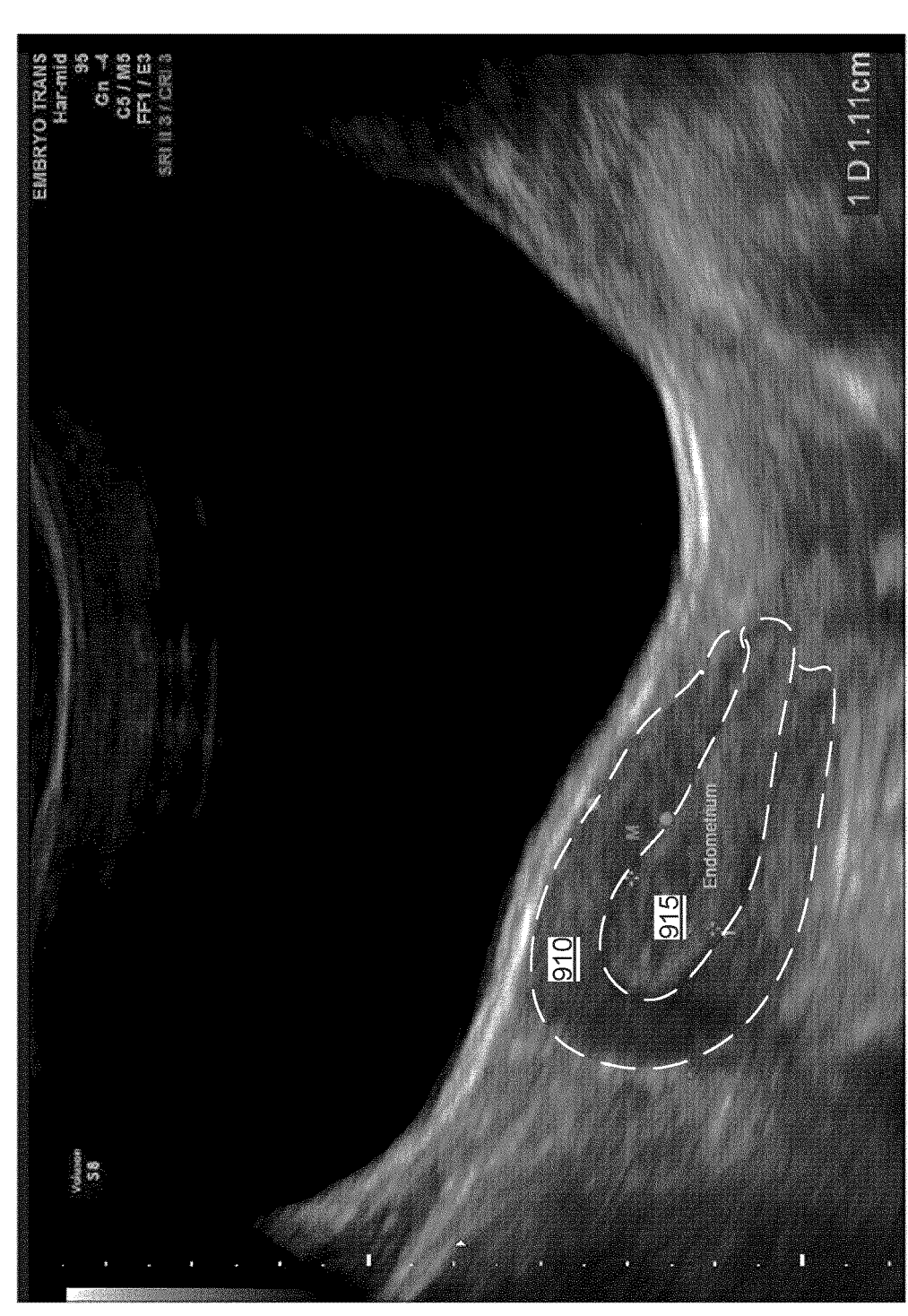
FIGS. 9A and 9B shows three example ultrasound images showing an endometrium, taken after treatment of progesterone and on the day of embryo transfer, in accordance with embodiments of the present disclosure.
Figure 9B:
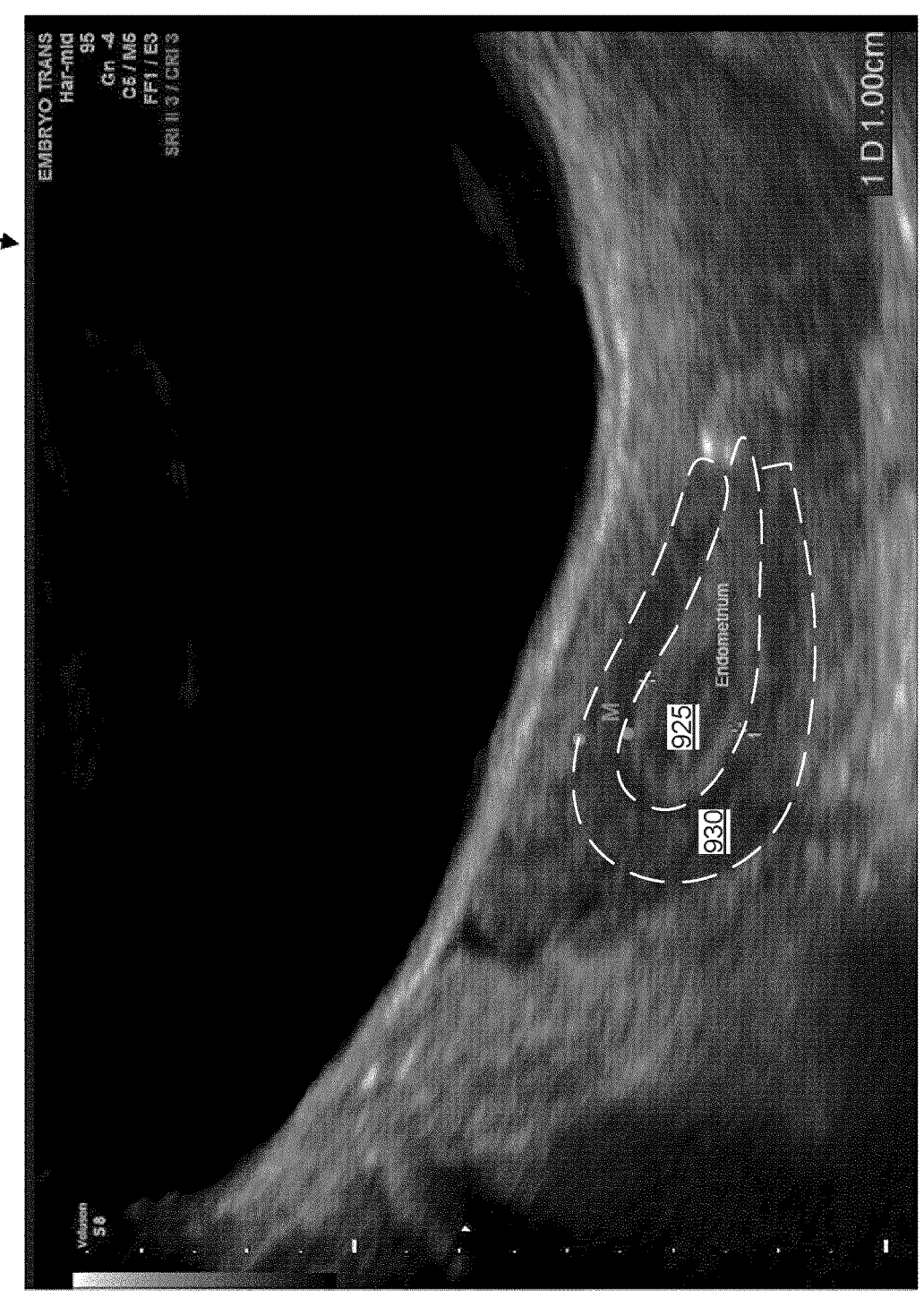

In some embodiments, the training data set may include all three types of ultrasound images: 1) a set of transvaginal ultrasound images taken 5-6 days before a planned embryo transfer (e.g., FIGS. 7A, 7B, 7C); 2) a set of transvaginal ultrasound images taken a day before a planned embryo transfer (e.g., FIGS. 8A, 8B); and 3) a set of abdominal ultrasound images taken on the day of the planned embryo transfer (e.g., FIGS. 9A, 9B).

Figure 7A:
FIGS. 7A to 7C shows three example ultrasound images showing an endometrium in the estrogen dominant phase (either a natural cycle or with hormonal medication such as estrogen), taken before treatment of progesterone, in accordance with embodiments of the present disclosure.
Figure 7B:
Figure 7C:
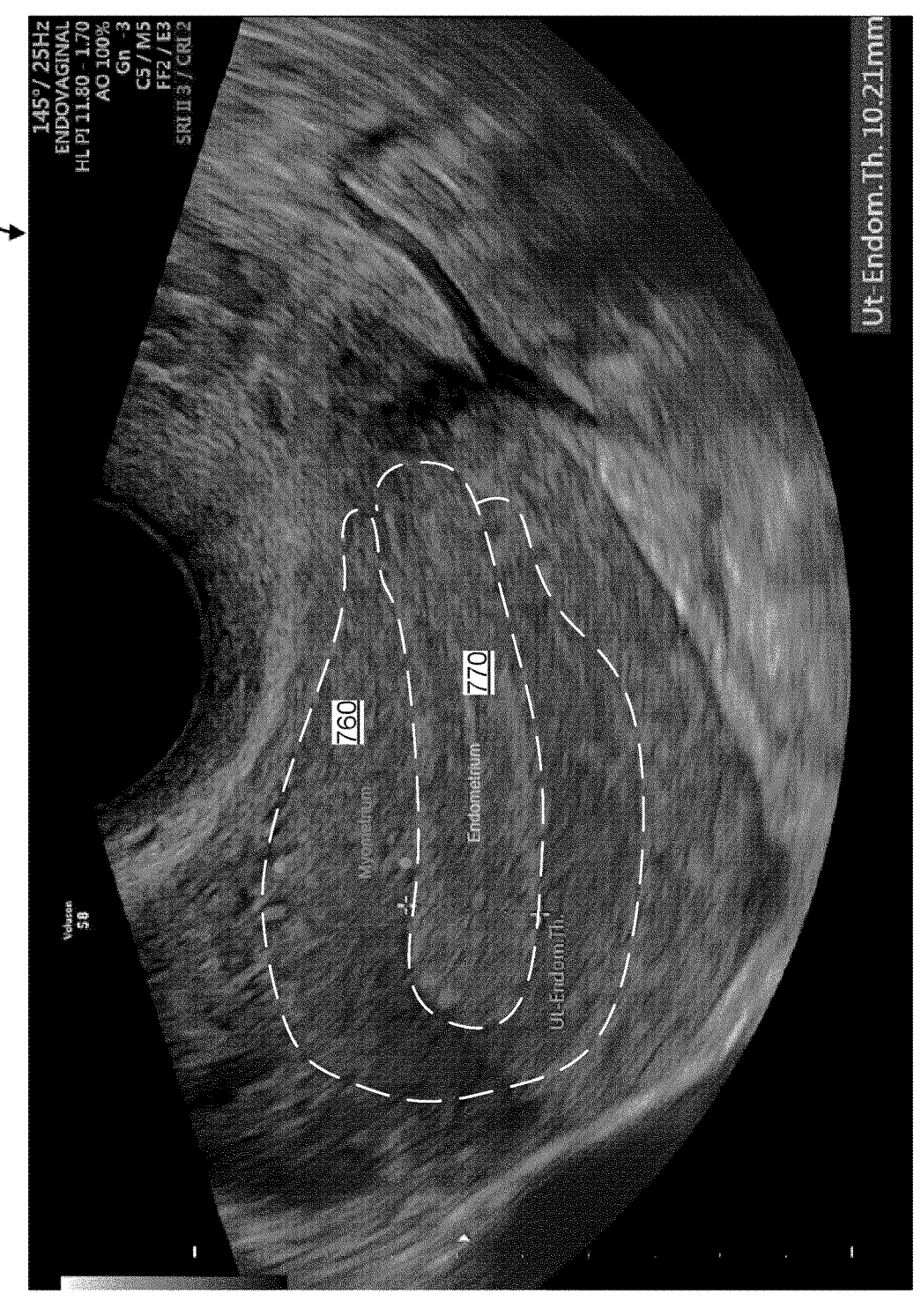

FIGS. 7A, 7B and 7C may be taken during either a natural cycle or with hormonal medication such as estrogen.

In some embodiments, auxiliary features, such as image masks, may be manually added to one or more ultrasound images in the training data set to help the neural network 110 learn faster and more efficiently. For example, image masks may be manually added to the plurality of ultrasound images to recognize one or more of: a trilaminar pattern, an endometrium surface area, and a myometrium area. Each of these image masks may assist with recognizing and extracting target endometrium features that may be used to generate a predicted value for endometrium receptivity.

In some embodiments, the ultrasound images are preprocessed before being included in the training data set, which may include the steps of: de-noising each image; removing images with potential information loss (too bright or too dark) via histogram analysis; normalizing brightness values; removing images that are too blurry; and removing markers and text from images that are not helpful for the machine learning algorithm to train the neural network 110.

In some embodiments, manual segmentation of ultrasound images may be performed to generate a segmentation dataset. Segmentation may refer to the task of labeling each pixel of a digital image as belonging to one of many classes (person, cat, airplane, table, etc.). The manual segmentation may divide a ultrasound image into different sections or areas: e.g., lining, surface area, and so on.

Next, the machine learning application 1120 may train a neural network, which may be neural network related to the neural network 110, based on the training data set using U-net++ or another suitable network to automatically segment images based on manually created masks and segments.

The machine learning application 1120 may then use one or more techniques to train CNN or another type of a neural network 110 to determine one or more target endometrium features, such as a thickness of the endometrium, for generating a predicted value for endometrium receptivity. The target endometrium features may indicate likelihood of an embryo's attachment and reaching clinical pregnancy.

In some embodiments, an example target endometrium feature may be a surface area of the endometrium enclosed by the fundal region superiorly, the internal cervix os inferiorly, and the two thickest points between the two basal layers on the anterior and posterior uterine walls. These points are meaningful points that are related to the characteristics of the endometrial morphology, namely the length and thickness of the endometrium.

In some embodiments, example target endometrium features may also include one or more of: a presence and clarity of a trilaminar pattern, an endometrium surface area, a myometrium area, an endometrium fundal region, an internal cervix os, and the two thickest points between the two basal layers on the anterior and posterior uterine walls.

The machine learning application 1120 may then use the one or more target endometrium features to train the neural network 110 to generate a predicted value for endometrium receptivity, by updating the plurality of weights for the neural network 112 during each training cycle.

As an optional step, the machine learning application 1120 may use data augmentation on images to improve network robustness: e.g., image flipping and rotating, prior to, or during extracting process of target endometrium features.

As a last, and optional step, the system 100 may add one or more clinical features to the generated outcome: pathology, patient age, preimplantation Genetic Testing for Aneuploidy (PGT-A), embryo score, date relative to initial embryo transfer and others.

Figure 4:
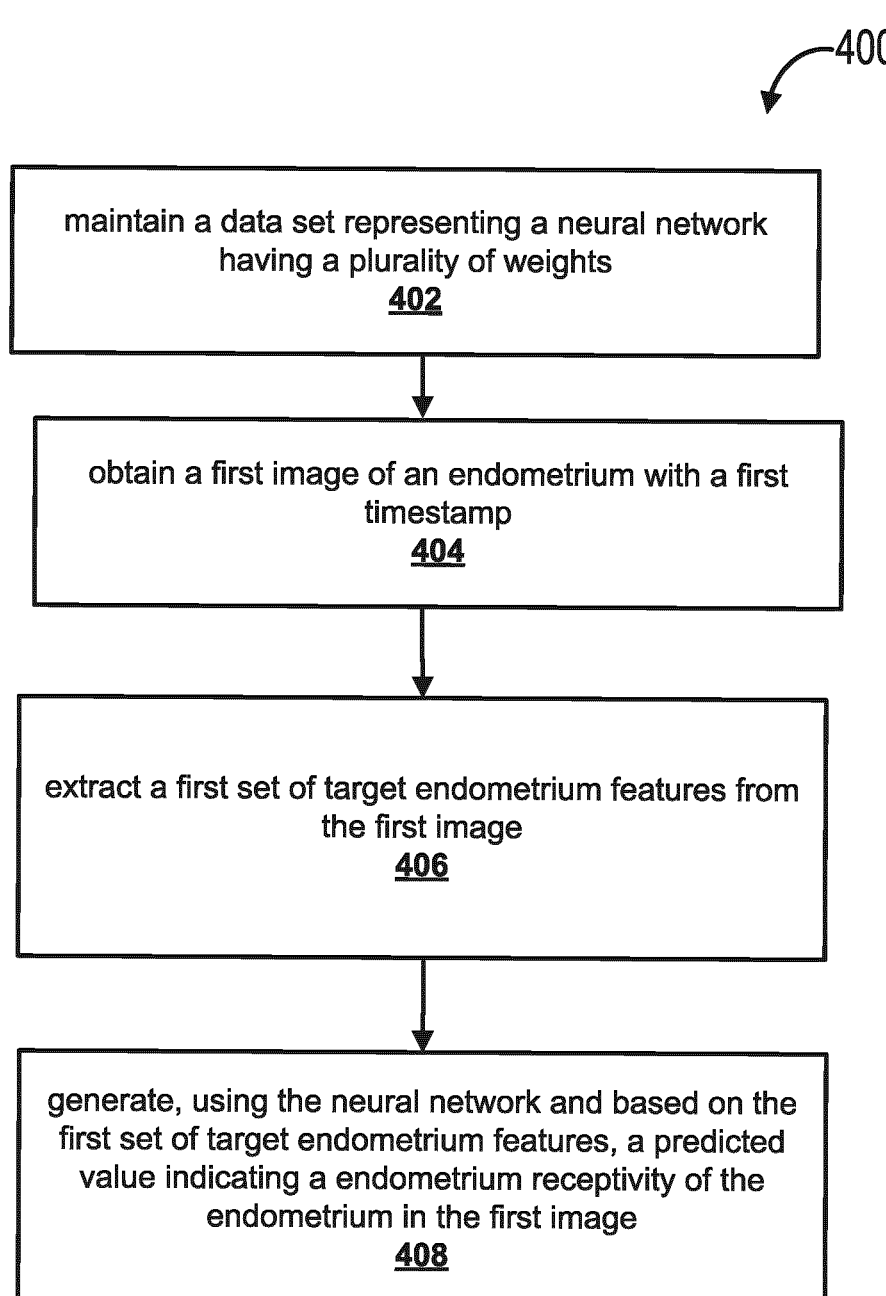
FIG. 4 illustrates a flowchart of a method for machine learning architecture for predicting endometrium receptivity, in accordance with embodiments of the present disclosure.

FIG. 4 illustrates a flowchart of a method 400 for machine learning architecture for predicting endometrium receptivity, in accordance with embodiments of the present disclosure. The method 400 may be conducted by the processor 104 of the system 100 in FIG. 1 or system 500 in FIG. 5 described below. Processor-executable instructions may be stored in the memory 108 and may be associated with the machine learning application 1120 or other processor-executable applications. The method 400 may include operations such as data retrievals, data manipulations, data storage, or other operations, and may include computer-executable operations.

At operation 402, the processor may maintain a data set representing a neural network 110 having a plurality of weights. The data set representing the neural network 110 may be stored, and the weights updated during each training iteration or training cycle.

At operation 404, the processor may obtain a first image of an endometrium of a patient, the first image having a first timestamp. The first image may be an ultrasound image from an ultrasound machine 160.

In some embodiments, the patient's endometrium to which the embryo may be added may also be referred to as a potential endometrium, that is, a potential endometrium which may be used in a reproductive process. In an exemplary embodiment, a clinician or a physician may be tasked with capturing images of a potential endometrium during a cycle. In an exemplary embodiment, the images may be focused on a window of implantation. As such, exemplary images that may be captured may indicate particular behavior and/or features of a specific potential endometrium through a reproductive cycle. A plurality of ultrasound images may be stored in one or more databases so that these may be compared to extracted features on a large dataset to predict when an embryo may be added to a uterus.

In an exemplary embodiment, an image of a potential endometrium may be captured utilizing an image capturing device, such as an ultrasound machine 160.

The first timestamp may indicate a certain period before the day of planned embryo transfer. For example, the first timestamp of the first image may indicate that the first image was taken 5 or 6 days before a planned embryo transfer, which can be the day before the patient starts a progesterone treatment.

In an exemplary embodiment, the image of the potential endometrium may be captured at various stages.

In an exemplary embodiment, settings and/or conditions for capturing an image of a potential endometrium may be kept the same or as consistently as possible. In an exemplary embodiment, images may be captured in grey scale. In an exemplary embodiment, image data may be manipulated and adjusted in order to capture all details of the subject to be captured. In an exemplary embodiment, the exposure may be adjusted so that all parts of the potential endometrium to be evaluated are clear.

In some embodiments, system 100 may perform image processing of the captured image data. Image processing of the captured image data may comprise cropping the captured image data so that the potential endometrium is the focus of the image and/or applying above-mentioned process of data augmentation. In an exemplary embodiment, the captured image may be cropped with the endometrium in the center. In an exemplary embodiment, an image of an object of interest (for example, a potential endometrium) may be at least 230 by 230 pixels after cropping.

In an exemplary embodiment, capturing an image of an object of interest, such as an endometrium may be conducted in similar manner and specification as capturing of the training data sets. In an exemplary embodiment, this may allow for more efficiency and accuracy in predictive accuracy of exemplary systems.

Each of FIGS. 7A, 7B and 7C shows an example transvaginal ultrasound image of the same endometrium (of the same patient) with measurements taken by an ultrasound technician, either during a natural cycle or with hormonal medication such as estrogen. Each image (without the indicated measurement by the ultrasound technician) can be used as a first image as input data to the neural network 110.

FIG. 7A shows a measurement of 10.79 mm for endometrium thickness in ultrasound image 700, FIG. 7B shows a measurement of 10.51 mm for endometrium thickness in ultrasound image 720, and FIG. 7C shows a measurement of 10.21 mm for endometrium thickness in ultrasound image 750. Therefore, as the ultrasound user interface 600 in FIG. 6 shows, an average value of 10.50 mm is taken as the final measurement 620 for endometrium thickness in this case.

At operation 406, the processor may extract a first set of target endometrium features from the first image. In some embodiments, the first set of target endometrium features comprises one or more: a thickness of the endometrium, a length of the endometrium, a surface area of the endometrium, the pattern (example trilaminar pattern), a myometrium area, an endometrium cavity tip (fundal region), an internal cervix os, and the two thickest points between the two basal layers on the anterior and posterior uterine walls.

FIGS. 7A to 9C each shows example features that may be extracted by the processor based on the ultrasound images.

FIG. 7A shows an example endometrium area 715 and a myometrium area 710 in the ultrasound image 700. FIG. 7B shows an example endometrium area 730 and a myometrium area 725 in the ultrasound image 720. FIG. 7C shows an example endometrium area 770 and a myometrium area 760 in the ultrasound image 750.

FIG. 8A shows an example endometrium area 815 and a myometrium area 810 in the ultrasound image 800. FIG. 8B shows an example endometrium area 830 and a myometrium area 825 in the ultrasound image 820.

FIG. 9A shows an example endometrium area 915 and a myometrium area 910 in the ultrasound image 900. FIG. 9B shows an example endometrium area 925 and a myometrium area 930 in the ultrasound image 920.

In some embodiments, other image or visual features may be automatically extracted by, for example, a CNN type neural network, based on importance for correctly predicting required outcome.

In some embodiments, prior to extracting the first set of target endometrium features, images may be processed by normalizing image brightness values, cropping irrelevant parts of an image, removing noise, or performing image sharpening.

The machine learning application 1120 may extract target endometrium features from the first image and if applicable, any subsequent second image(s). For example, based on extracted features of the first image, it may be determined what features indicate likelihood of reproductive milestones, such as implantation, or lack thereof.

At operation 406, the processor may generate, using the neural network and based on the first set of target endometrium features, a predicted value indicating a endometrium receptivity of the endometrium in the first image. The predicted value may be, for example, a probability value P % indicating that the endometrium receptivity is P % (e.g., 80%) likely to result in a successful embryo implantation.

In some embodiments, the processor can: generate a value representative of a likelihood of a successful embryo implantation. The system 100 may, through machine learning application 1120, generate a value indicating a likelihood of reaching each of the reproductive milestones of the potential embryo based on the extracted features and the image. Specifically, a likelihood in terms of percentage, a ranking, or a numerical value may be calculated for embryo implantation and clinical pregnancy. In an exemplary embodiment, a simple prediction regarding each reproductive milestone may be made.

In some embodiments, the predicted value indicating an endometrium receptivity of the endometrium in the first image needs to exceed a predefined threshold (e.g., 79.99%) in order for the system 100 to generate a value representative of a positive likelihood of a successful embryo implantation.

In some embodiments, the processor can: receive a second image of the endometrium with a second timestamp; extract a second set of target endometrium features from the second image; and generate, using the neural network and based on the first and second sets of target endometrium features, the predicted value indicating the endometrium receptivity of the endometrium.

For example, a second image of a patient's endometrium may be taken in a clinical setting at a later date than the first timestamp, to determine likelihood of reaching each of the reproductive milestones for an embryo if its introduced in a uterus within a specific time period.

The system 100 may provide a timeline for determining based on endometrium features when the embryo may be implanted. For example, based on features, it may be determined that the embryo may be implanted the same day or at a time period, such as two days, from the indication.

Each of FIGS. 8A and 8B shows an example transvaginal ultrasound image of the same endometrium (of the same patient) with measurements taken by an ultrasound technician. Each image (without the indicated measurement by the ultrasound technician) can be used as a second image as input data to the neural network 110. FIG. 8A shows a measurement of 1.19 cm or 11.9 mm for endometrium thickness in ultrasound image 800, and FIG. 8B shows a measurement of 1.16 cm or 11.6 mm for endometrium thickness in ultrasound image 820. These second images are associated with a timestamp that is a day before the planned embryo transfer, which means that these images are taken about 4 days after the first images shown in FIGS. 7A and 7B.

In some embodiments, instead of, or in addition to, using the transvaginal ultrasound images taken the day before planned embryo transfer (e.g., FIGS. 8A, 8B), the second image may include abdominal ultrasound images taken on the day of planned embryo transfer. Each of FIGS. 9A and 9B shows an example abdominal ultrasound image of the same endometrium (of the same patient) with measurements taken by an ultrasound technician, on the day of the planned embryo transfer. Each image (without the indicated measurement by the ultrasound technician) can be used as a second image as input data to the neural network 110. FIG. 9A shows a measurement of 1.11 cm or 11.1 mm for endometrium thickness in ultrasound image 900, FIG. 9B shows a measurement of 1.00 cm or 10.0 mm for endometrium thickness in ultrasound image 920. These second images are associated with a timestamp that is a day before the planned embryo transfer, which means that these images are taken about 5 days after the first images shown in FIGS. 7A and 7B.

In some embodiments, the second set of target endometrium features comprises at least one of: a thickness of the endometrium, a length of the endometrium, a surface area of the endometrium, a trilaminar pattern, a myometrium area, an endometrium cavity tip, an internal cervix os, and the two thickest points between the two basal layers on the anterior and posterior uterine walls.

For example, as shown in FIG. 8B, there is a trilaminar pattern within the endometrium. The trilaminar pattern shows an inner uterine lining that has a triple-line pattern as seen on an ultrasound examination. This type of endometrium is typically thick and receptive enough to aid in successful embryo implantation.

In some embodiments, the processor can determine a difference between the first image and the second image; and analyze the difference to generate the predicted value indicating the endometrium receptivity of the endometrium. For example, comparing FIG. 7C (example first image) to FIG. 8A (example second image), the endometrium thickness increased from 10.21 mm to 11.9 mm, which can be taken as an indication of a positive trend towards a higher endometrium receptivity value.

For another example, the trilaminar pattern in FIG. 8A has thicker lining walls than in FIG. 7C, which may be another indication of a positive trend towards a higher endometrium receptivity value.

In an exemplary embodiment, the result may indicate whether a potential embryo should be transferred, whether a further delay in transferring is warranted, or whether transfer should be attempted in a later cycle.

In some embodiments, the first image and the second image are transvaginal ultrasound images.

In some embodiments, the first image is a transvaginal ultrasound image and the second image is an abdominal ultrasound image.

Figure 5:
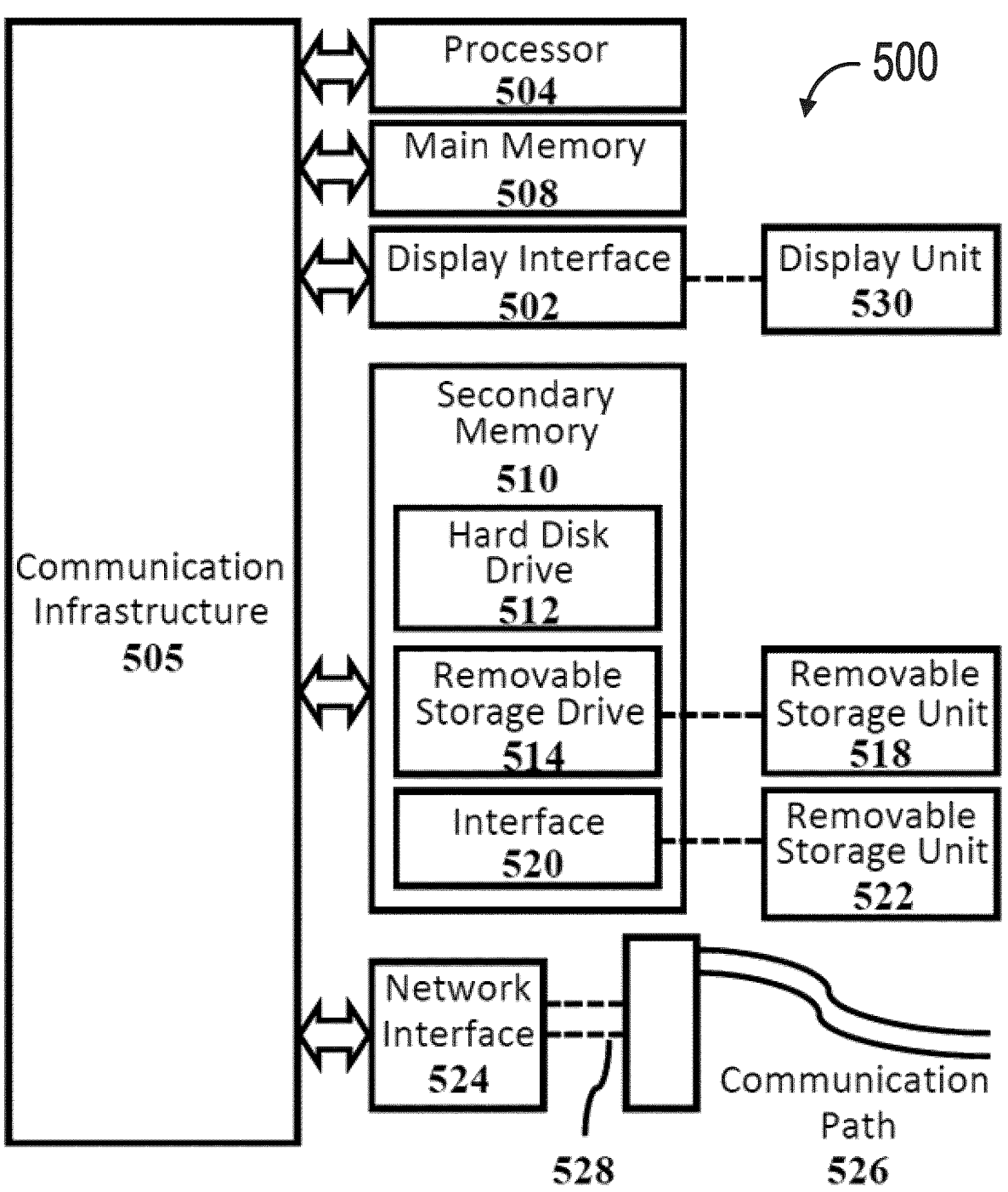
FIG. 5 illustrates another example computer system for predicting endometrium receptivity, in accordance with embodiments of the present disclosure.

FIG. 5 illustrates another example computer system 500 in which an embodiment of the present disclosure, or portions thereof, may be implemented as computer-readable code, consistent with exemplary embodiments of the present disclosure. For example, computer system 500 may include hardware, software, firmware, tangible computer readable media having instructions stored thereon, or a combination thereof and may be implemented in one or more computer systems or other processing systems. Hardware, software, or any combination of such may embody any of the modules and components utilized with respect to the process described in FIG. 4.

If programmable logic is used, such logic may execute on a commercially available processing platform or a special purpose device. One of ordinary skill in the art may appreciate that an embodiment of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device.

For instance, a computing device having at least one processor device and a memory may be used to implement the above-described embodiments. A processor device may be a single processor, a plurality of processors, or combinations thereof. Processor devices may have one or more processor "cores."

An embodiment of the invention is described in terms of this example computer system 500. After reading this description, it will become apparent to a person skilled in the relevant art how to implement the invention using other computer systems and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

Processor device 504 may be a special purpose or a general-purpose processor device. As will be appreciated by persons skilled in the relevant art, processor device 504 may also be a single processor in a multi-core/multiprocessor system, such system operating alone, or in a cluster of computing devices operating in a cluster or server farm. Processor device 504 is connected to a communication infrastructure 505, for example, a bus, message queue, network, or multi-core message-passing scheme.

Computer system 500 also includes a main memory 508, for example, random access memory (RAM), and may also include a secondary memory 510. Secondary memory 510 may include, for example, a hard disk drive 512, removable storage drive 514. Removable storage drive 514 may comprise a floppy disk drive, a magnetic tape drive, an optical disk drive, a flash memory, or the like. The removable storage drive 514 reads from and/or writes to a removable storage unit 518 in a well-known manner. Removable storage unit 518 may comprise a floppy disk, magnetic tape, optical disk, etc., which is read by and written to by removable storage drive 514. As will be appreciated by persons skilled in the relevant art, removable storage unit 518 includes a computer usable storage medium having stored therein computer software and/or data.

In alternative implementations, secondary memory 510 may include other similar means for allowing computer programs or other instructions to be loaded into computer system 500. Such means may include, for example, a removable storage unit 522 and an interface 520. Examples of such means may include a program cartridge and cartridge interface (such as that found in video game devices), a removable memory chip (such as an EPROM, or PROM) and associated socket, and other removable storage units 522 and interfaces 520 which allow software and data to be transferred from the removable storage unit 522 to computer system 500.

Computer system 500 may also include a communications interface 524. Communications interface 524 allows software and data to be transferred between computer system 500 and external devices. Communications interface 524 may include a modem, a network interface (such as an Ethernet card), a communications port, a PCMCIA slot and card, or the like. Software and data transferred via communications interface 524 may be in the form of signals, which may be electronic, electromagnetic, optical, or other signals capable of being received by communications interface 524. These signals may be provided to communications interface 524 via a communications path 526. Communications path 526 carries signals and may be implemented using wire or cable, fiber optics, a phone line, a cellular phone link, an RF link or other communications channels.

In this document, the terms "computer program medium" and "computer usable medium" are used to generally refer to media such as removable storage unit 518, removable storage unit 522, and a hard disk installed in hard disk drive 512. Computer program medium and computer usable medium may also refer to memories, such as main memory 508 and secondary memory 510, which may be memory semiconductors (e.g. DRAMs, etc.).

Computer programs (also called computer control logic) are stored in main memory 508 and/or secondary memory 510. Computer programs may also be received via communications interface 524. Such computer programs, when executed, enable computer system 500 to implement the present invention as discussed herein. In particular, the computer programs, when executed, enable processor device 504 to implement the processes of the present invention, such as the operations in the method 400 illustrated by FIG. 4 discussed above. Accordingly, such computer programs represent controllers of the computer system 500. Where the invention is implemented using software, the software may be stored in a computer program product and loaded into computer system 500 using removable storage drive 514, interface 520, and hard disk drive 512, or communications interface 524.

Embodiments of the invention also may be directed to computer program products comprising software stored on any computer useable medium. Such software, when executed in one or more data processing device, causes a data processing device(s) to operate as described herein. An embodiment of the invention employ any computer useable or readable medium. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, and optical storage devices, MEMS, nanotechnological storage device, etc.).

The embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments but should be defined only in accordance with the following claims and their equivalents.

Throughout this specification and the claims which follow, unless the context requires otherwise, the word "comprise", and variations such as "comprises" or "comprising", will be understood to imply the inclusion of a stated integer or step or group of integers or steps but not to the exclusion of any other integer or step or group of integers or steps.

Moreover, the word "substantially" when used with an adjective or adverb is intended to enhance the scope of the particular characteristic; e.g., substantially planar is intended to mean planar, nearly planar and/or exhibiting characteristics associated with a planar element. Further use of relative terms such as "vertical", "horizontal", "up", "down", and "side-to-side" are used in a relative sense to the normal orientation of the apparatus.

The term "connected" or "coupled to" may include both direct coupling (in which two elements that are coupled to each other contact each other) and indirect coupling (in which at least one additional element is located between the two elements).

Although the embodiments have been described in detail, it should be understood that various changes, substitutions and alterations can be made herein without departing from the scope. Moreover, the scope of the present disclosure is not intended to be limited to the particular embodiments of the process, machine, manufacture, composition of matter, means, methods and steps described in the specification.

As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized. Accordingly, the appended claims are intended to include within their scope such processes, machines, manufacture, compositions of matter, means, methods, or steps.

The description provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

The embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface.

Program code is applied to input data to perform the functions described herein and to generate output information. The output information is applied to one or more output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof.

Throughout the foregoing discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The technical solution of embodiments may be in the form of a software product. The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods provided by the embodiments.

The embodiments described herein are implemented by physical computer hardware, including computing devices, servers, receivers, transmitters, processors, memory, displays, and networks. The embodiments described herein provide useful physical machines and particularly configured computer hardware arrangements.

As can be understood, the examples described above and illustrated are intended to be exemplary only.

Applicant notes that the described embodiments and examples are illustrative and non-limiting. Practical implementation of the features may incorporate a combination of some or all of the aspects, and features described herein should not be taken as indications of future or existing product plans. Applicant partakes in both foundational and applied research, and in some cases, the features described are developed on an exploratory basis.

The invention claimed is:

1. A computer-implemented system for predicting endometrium receptivity, comprising:
    a processor; and a memory coupled to the processor and storing processor-executable instructions that, when executed, configure the processor to:
        maintain a data set representing a neural network having a plurality of weights;
        obtain a first image of an endometrium with a first timestamp;
        extract a first set of target endometrium physical features from the first image, including a thickness of the endometrium, wherein extracting the thickness of the endometrium comprises identifying morphologically-relevant points of the endometrium in the first image and determining the thickness of the endometrium based on at least some of the morphologically-relevant points; and
        generate, using the neural network and based on the first set of target endometrium physical features including the thickness of the endometrium, a predicted value indicating an endometrium receptivity for embryo implantation in the endometrium in the first image, the predicted value for determining a window of the embryo implantation.

2. The system of claim 1, wherein the processor-executable instructions, when executed, further configure the processor to:
    generate a value representative of a likelihood of a successful embryo implantation.

3. The system of claim 1, wherein the first set of target endometrium physical features further comprises at least one of: a length of the endometrium, a surface area of the endometrium, and a pattern of the endometrium.

4. The system of claim 3, wherein the pattern of the endometrium comprises a trilaminar pattern.

5. The system of claim 1, wherein the processor-executable instructions, when executed, configure the processor to:
    receive a second image of the endometrium with a second timestamp;
    extract a second set of target endometrium physical features from the second image; and
    generate, using the neural network and based on the first and second sets of target endometrium physical features, the predicted value indicating the endometrium receptivity for embryo implantation in the endometrium.

6. The system of claim 5, wherein the second set of target endometrium physical features comprises at least one of: a thickness of the endometrium, a length of the endometrium, a surface area of the endometrium, and a trilaminar pattern of the endometrium.

7. The system of claim 5, wherein the processor-executable instructions, when executed, configure the processor to:
    determine a difference between the first image and the second image; and
    analyze the difference to generate the predicted value indicating the endometrium receptivity for embryo implantation in the endometrium.

8. The system of claim 1, wherein the predicted value indicating the endometrium receptivity comprises a probability value.

9. The system of claim 1, wherein the neural network is trained based on a set of training data comprising:
    a plurality of ultrasound images of one or more endometria, each of the plurality of ultrasound images showing a respective endometrium; and
    for each of the plurality of ultrasound images, a respective label indicating an outcome of a respective embryo implantation in the respective endometrium in the respective ultrasound image.

10. The system of claim 9, wherein each of the plurality of ultrasound images is associated with training data comprising a blastocyst quality of an embryo transferred into a respective endometrial cavity in the respective ultrasound image.

11. A computer-implemented method for predicting endometrium receptivity, the method comprising:

maintaining a data set representing a neural network having a plurality of weights;

obtaining a first image of an endometrium with a first timestamp;

extracting a first set of target endometrium physical features from the first image including a thickness of the endometrium, wherein extracting the thickness of the endometrium comprises identifying morphologically-relevant points of the endometrium in the first image and determining the thickness of the endometrium based on at least some of the morphologically-relevant points; and generating, using the neural network and based on the first set of target endometrium physical features including the thickness of the endometrium, a predicted value indicating an endometrium receptivity for embryo implantation in the endometrium in the first image, the predicted value for determining a window of the embryo implantation.

12. The method of claim 11, further comprising:

generating a value representative of a likelihood of a successful embryo implantation.

13. The method of claim 11, wherein the first set of target endometrium physical features further comprises at least one of: a length of the endometrium, a surface area of the endometrium, and a pattern of the endometrium.

14. The method of claim 13, wherein the pattern of the endometrium comprises a trilaminar pattern.

15. The method of claim 11, further comprising:

receiving a second image of the endometrium with a second timestamp;

extracting a second set of target endometrium physical features from the second image; and generating, using the neural network and based on the first and second sets of target endometrium physical features, the predicted value indicating the endometrium receptivity of the endometrium.

16. The method of claim 15, wherein the second set of target endometrium features comprises at least one of: a thickness of the endometrium, a length of the endometrium, a surface area of the endometrium, and a trilaminar pattern of the endometrium.

17. The method of claim 15, further comprising:

determining a difference between the first image and the second image; and analyzing the difference to generate the predicted value indicating the endometrium receptivity of the endometrium.

18. The method of claim 11, wherein the neural network is trained based on a set of training data comprising:

a plurality of ultrasound images of one or more endometria, each of the plurality of ultrasound images showing a respective endometrium; and for each of the plurality of ultrasound images, a respective label indicating an outcome of a respective embryo implantation in the respective endometrium in the respective ultrasound image.

19. The method of claim 18, wherein each of the plurality of ultrasound images is associated with training data comprising a blastocyst quality of an embryo transferred into a respective endometrial cavity in the respective ultrasound image.

20. A non-transitory computer-readable medium having stored thereon machine interpretable instructions which, when executed by a processor, cause the processor to perform:

maintaining a data set representing a neural network having a plurality of weights;

obtaining a first image of an endometrium with a first timestamp;

extracting a first set of target endometrium physical features from the first image including a thickness of the endometrium, wherein extracting the thickness of the endometrium comprises identifying morphologically-relevant points of the endometrium in the first image and determining the thickness of the endometrium based on at least some of the morphologically-relevant points; and generating, using the neural network and based on the first set of target endometrium physical features including the thickness of the endometrium, a predicted value indicating a endometrium receptivity for embryo implantation in the endometrium in the first image, the predicted value for determining a window for the embryo implantation.

* * * * *